United States Patent
Claussen

(10) Patent No.: US 6,789,044 B2
(45) Date of Patent: *Sep. 7, 2004

(54) METHOD AND APPARATUS FOR DETERMINING A NECK MOVEMENT PATTERN

(75) Inventor: Claus-F. Claussen, Bad Kissingen (DE)

(73) Assignee: Claus-Frenz Claussen, Bad Kissingen (DE)

( * ) Notice: Subject to any disclaimer, the term of this patent is extended or adjusted under 35 U.S.C. 154(b) by 375 days.

This patent is subject to a terminal disclaimer.

(21) Appl. No.: 10/034,918

(22) Filed: Oct. 22, 2001

(65) Prior Publication Data

US 2002/0116990 A1 Aug. 29, 2002

Related U.S. Application Data

(63) Continuation of application No. PCT/EP00/03378, filed on Apr. 14, 2000.

(30) Foreign Application Priority Data

Apr. 21, 1999 (DE) .......................................... 199 18 008

(51) Int. Cl.[7] .............................................. G01C 17/00
(52) U.S. Cl. ........................ 702/152; 702/150; 702/151; 702/153; 600/594; 600/595
(58) Field of Search ................................ 702/152, 150, 702/151, 153; 600/594, 595

(56) References Cited

U.S. PATENT DOCUMENTS

| | | | | |
|---|---|---|---|---|
| 4,528,990 A | * | 7/1985 | Knowles | 600/595 |
| 5,086,404 A | * | 2/1992 | Claussen | 356/139.03 |
| 5,203,346 A | * | 4/1993 | Fuhr et al. | 600/594 |
| 6,473,717 B1 | * | 10/2002 | Claussen et al. | 702/153 |
| 6,514,219 B1 | * | 2/2003 | Guimond et al. | 600/595 |

FOREIGN PATENT DOCUMENTS

| | | |
|---|---|---|
| DE | 38 29 885 A1 | 3/1990 |
| WO | WO 91/01514 | 2/1991 |

* cited by examiner

*Primary Examiner*—John Barlow
*Assistant Examiner*—Anthony T. Dougherty
(74) *Attorney, Agent, or Firm*—Laurence A. Greenberg; Werner H. Stemer; Ralph E. Locher

(57) ABSTRACT

A pattern is determined of the neck movement of a subject. The head/body movement of the subject is recorded with markers placed on the shoulders and on the head and thus moving with the subject. The locus curve of each marker in three-dimensional space is then determined in dependence on the time and it is stored as a data set. The neck movement is isolated from the head and torso movements by determining the difference between the average of the two locus curves that represent the shoulder movements and the locus curve representing the head movement. The pattern of movement established on the cranio-corpo-graphy is evaluated and analyzed using a data-processing device. The method is particularly suitable for determining the presence and the severity of an injury to the cervical spine as a result of whiplash caused by a traffic accident.

11 Claims, 10 Drawing Sheets

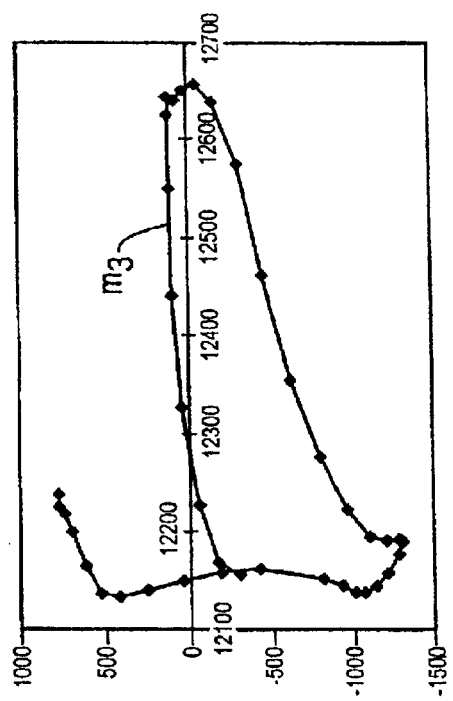
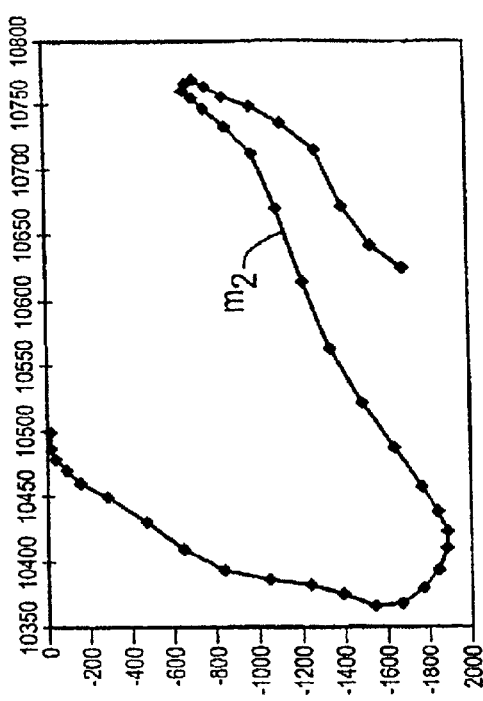
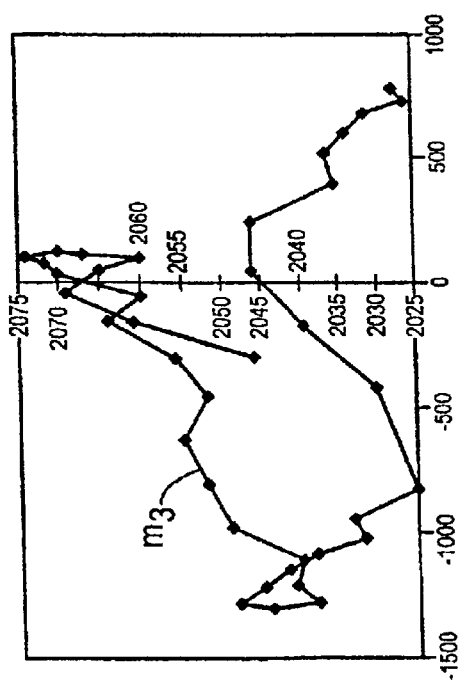
Fig. 2.1
Fig. 2.2
Fig. 2.3
Fig. 2.4

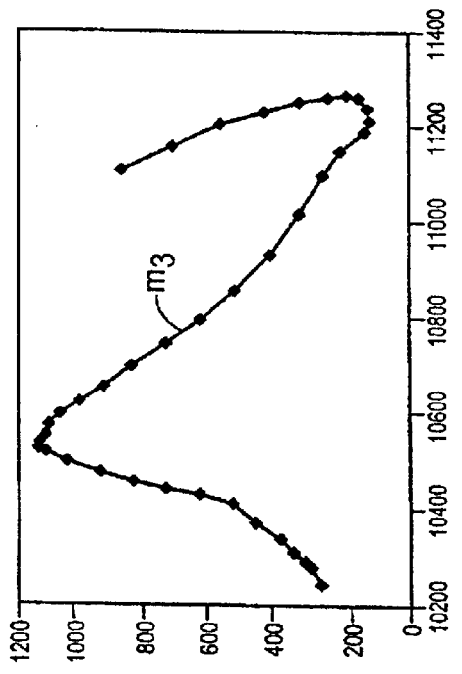
Fig. 3.2
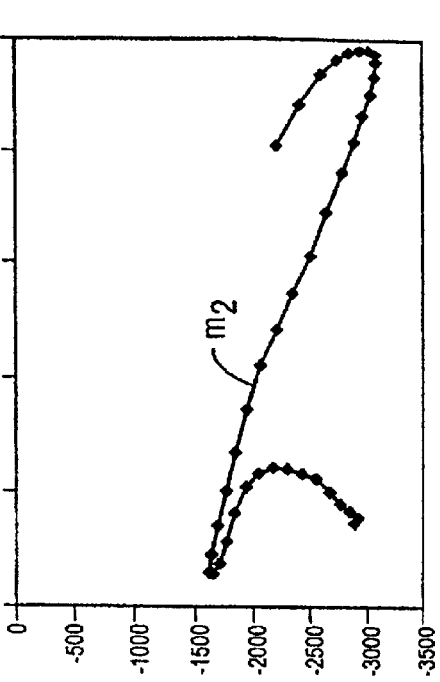
Fig. 3.4
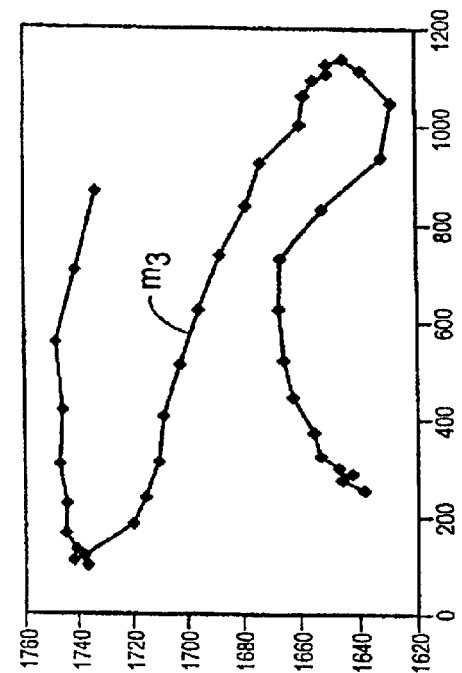
Fig. 3.1
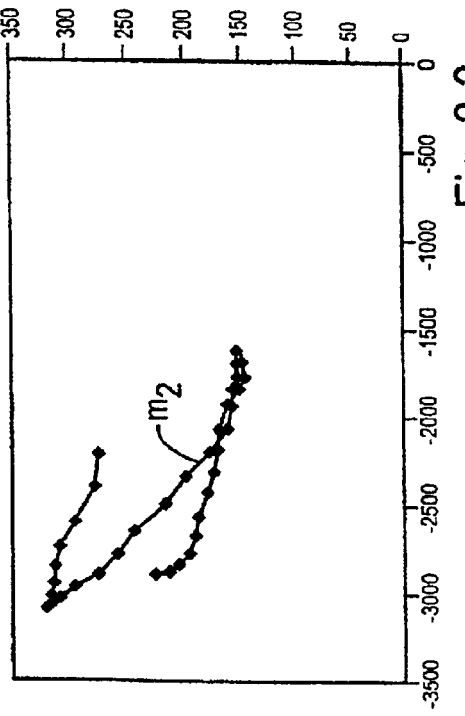
Fig. 3.3

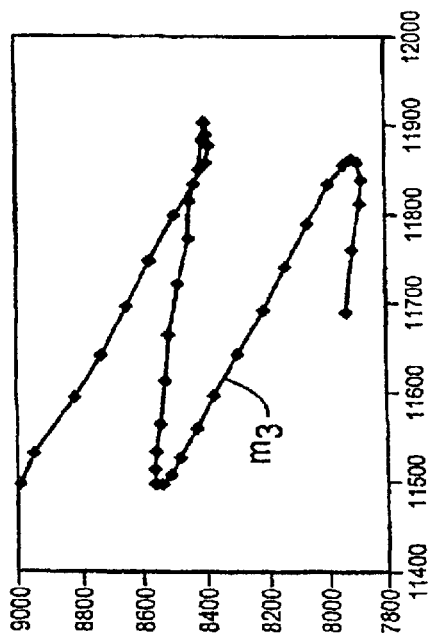
Fig. 4.1
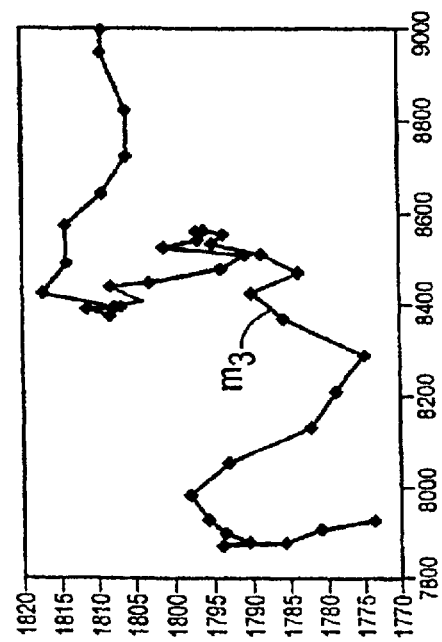
Fig. 4.3
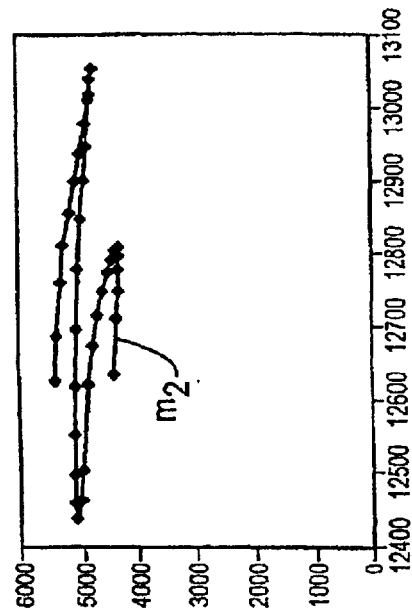
Fig. 4.2
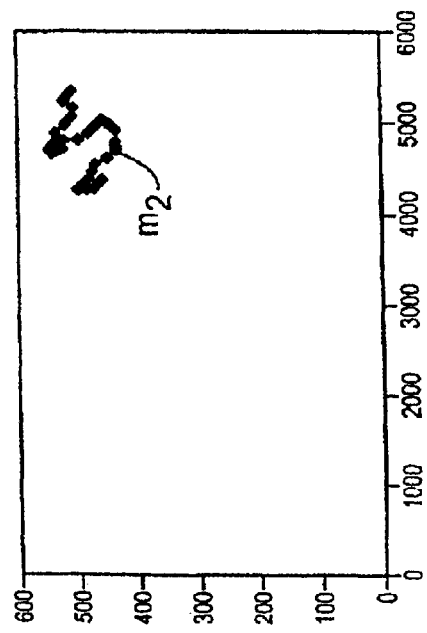
Fig. 4.4

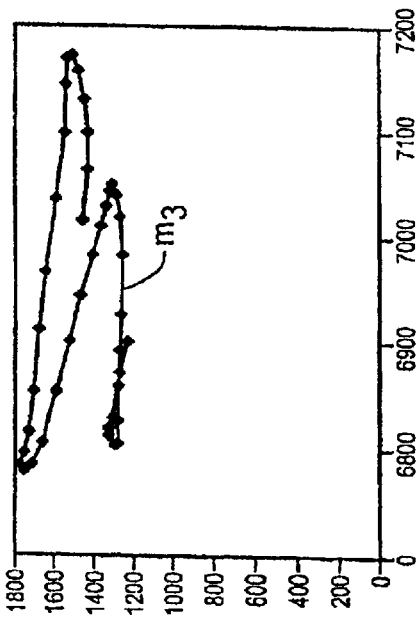
Fig. 5.1
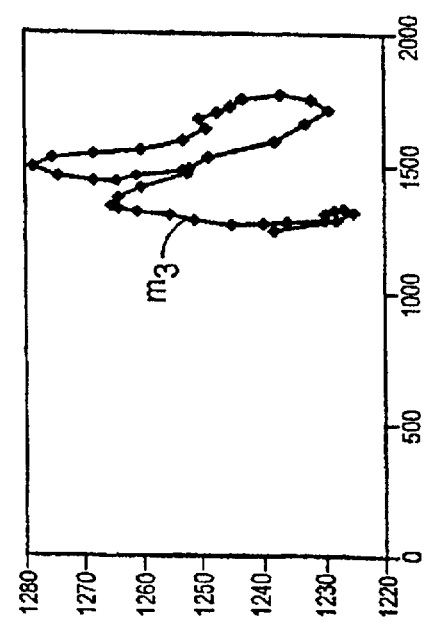
Fig. 5.2
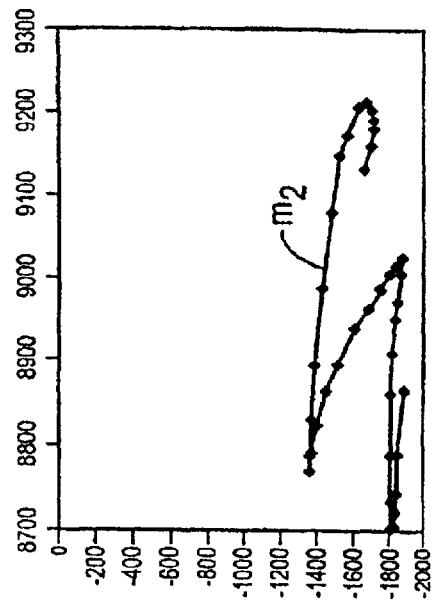
Fig. 5.3
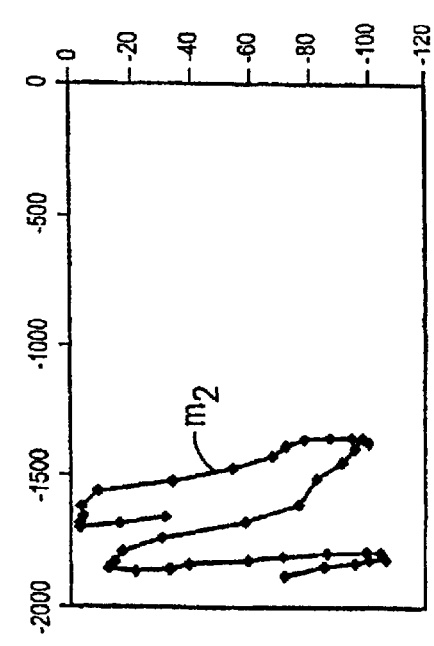
Fig. 5.4

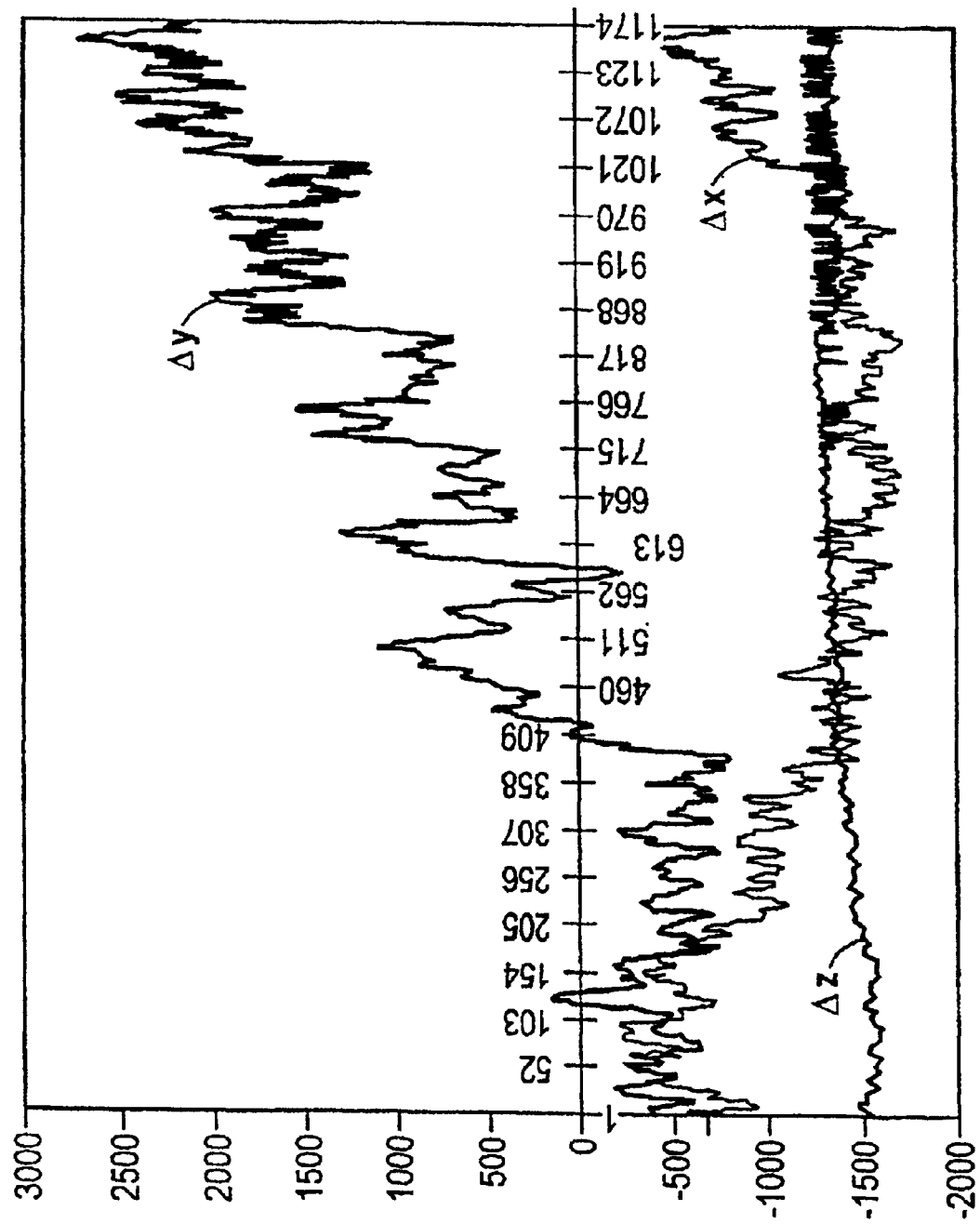

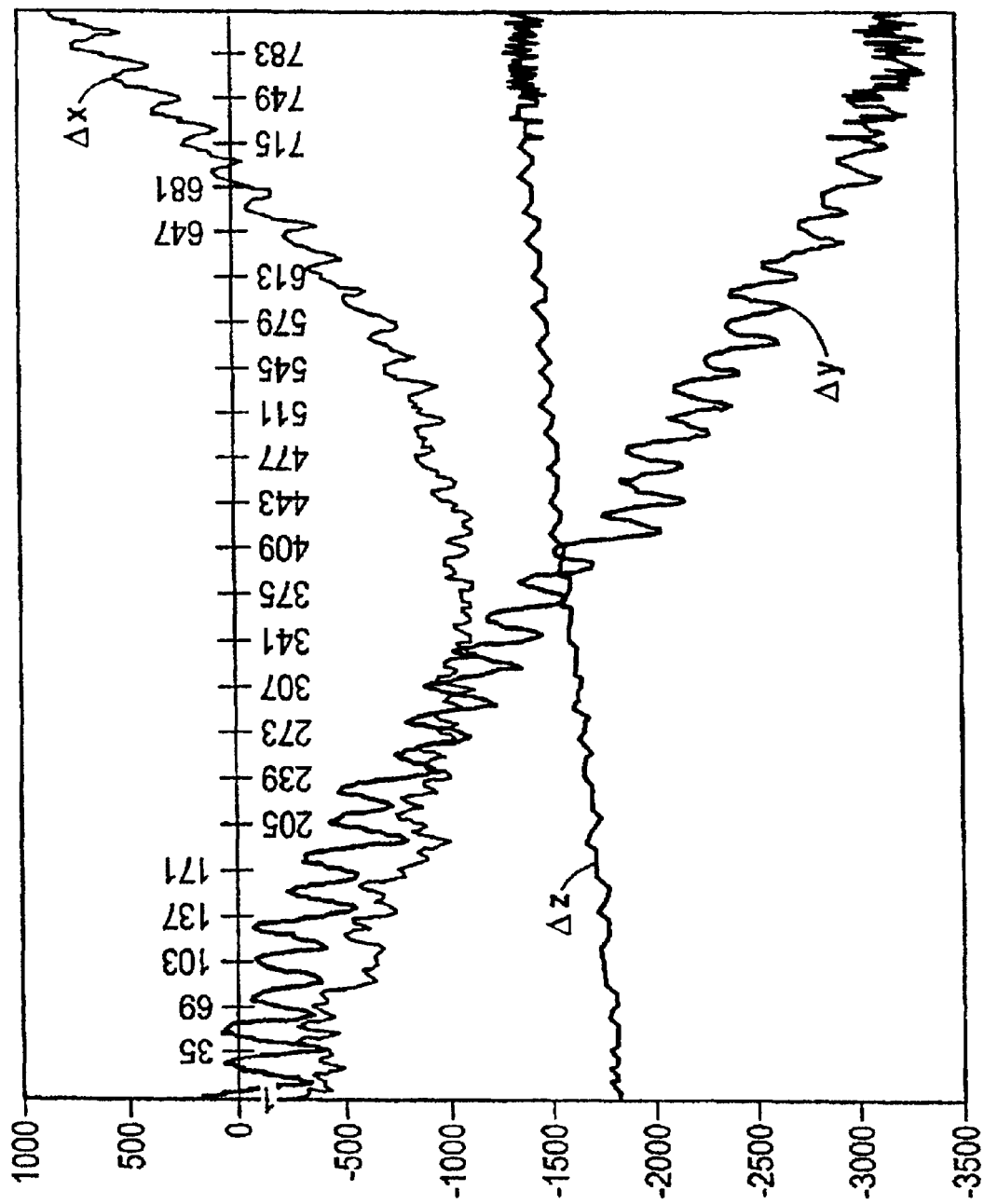

METHOD AND APPARATUS FOR DETERMINING A NECK MOVEMENT PATTERN

CROSS-REFERENCE TO RELATED APPLICATION

This application is a continuation of copending International Application No. PCT/EP00/03378, filed Apr. 14, 2000, which designated the United States.

BACKGROUND OF THE INVENTION

Field of the Invention

The invention relates to a method for determining the neck movement pattern of a subject. It also relates to a corresponding apparatus for carrying out the method.

It has long been desired to find a suitable examination method in order to be able to measure reliably impairments of neck mobility resulting from a head-neck whiplash injury, termed a cervical column whiplash injury. The principal object of the examination methods or procedures that are to be applied in the physical and functional fields with the focus on symptoms and individual cases is to clarify accident-related injuries in the region of the cervical column.

The cervical column whiplash injury, which counts among the most frequent traumatic injuries of the neck, is a pathological injury that occurs, in particular, as a result of automobile accidents with or without contact with the inside of the vehicle. The cervical column whiplash injury here denotes a physical acceleration or deceleration traumatic injury with a transfer of energy to the head-neck structure, which is connected similarly to a pendulum rod, with a rotary-sliding joint, specifically the head socket joint, mounted on top. The flinging movements can be initiated by linear rear and/or front impact accidents, or by linear impact accidents on the right-hand or left-hand side. Also known, in addition, are comparatively complicated collision mechanisms wherein the vehicles are hit diagonally.

The diagonal collisions generally result in a rotation of the vehicle accompanied by angular rotational accelerations which continue on to the cervical column structure, its joints, ligaments, muscles, tendons and other movement articulations of the or each vehicle occupant. The cervical column whiplash injury is therefore distinguished by a multifarious set of symptoms which frequently can be predicted only with difficulty in the individual case owing to the traumatic injury that is acting. In this regard, various terms are used in the medical literature to describe this injury such as, for example, cervico-encephalic, cervico-brachial, cervico-medullary or cervical syndrome, chronic post-traumatic head/neck injury, cervical column distortion, or whiplash syndrome.

Since the neck region is traversed not only by the spinal cord as the important central nervous control organ, but also by important blood vessels, nerve pathways, muscles, tendons, the esophagus and windpipe, injury in this region can lead to particularly severe medical conditions determined by a multiplicity of symptoms. As a result of the multiplicity of these many symptoms and syndromes, there has so far not been any diagnostic finding which can be established in a simple way and is at the same time reliable and can conclusively prove the cervical column whiplash injury per se.

A first proof has been achieved through a radiological determination of the ligament injuries inside the head socket joint, that is to say the connections between the cranial base and the first and second cervical vertebrae. This involves nuclear magnetic resonance imaging which can, however, in the final analysis ascertain only relatively major morphological injuries such as ligament ruptures, torn ligaments, ligament swelling and eccentricities and/or fractures of the dens axis.

Those affected (the patients) themselves note the substantial changes in the head socket joint after the collision with a vehicle because they acquire a stiff neck or suffer neck pain and are greatly limited in their head-neck mobility.

U.S. Pat. No. 5,203,346 (see international PCT publication WO 91/15148 (PCT/US91/01796)) describes a noninvasive method for determining the movement of the cervical vertebrae. There, a subject in a sitting position is instructed to follow visual stimuli and, systematically, a luminous marking pattern on a wall while his head movements are recorded in three dimensions by means of video cameras. For this purpose, a marking device which can be recorded is fitted on the head of the subject. If deviations from the straight sequence of luminous simulators are determined, these deviations are interpreted as faulty control of the neck movements.

Although the examination is carried out on a seated patient, it is, on the one hand, not ensured in this known method that the patient or subject behaves during the head movement in such a way that no additional head and trunk movements occur which under natural conditions support targeted head movement. On the other hand, the seated position disadvantageously leads to a restriction of the movement of the subject. Since trunk movements supporting the head movement are therefore not taken into account, and it is only from the acquired head movement that conclusions are drawn concerning the movement or mobility of the cervical column without, moreover, distinguishing between the lower cervical column (pendulum rod) and upper cervical column (head socket joint), the known method is not sufficiently exact, particularly with regard to a reliable statement on the type and degree, as well as the localization, of an injury to the cervical column. Consequently, this known method cannot be used, at least not in the way desired, to prove on good foundations the causality of an injury to the cervical column as a consequence of a cervical column whiplash injury caused by a traffic accident.

In the case of a device known from the printed publication entitled "Forschungsbericht Cranio-Corpo-Grafie (CCG)", ISBN 3-88383-126-3 (June 1986) appearing in the series of papers of the Hauptverband der gewerblichen Berufsgenossenschaften e.V., the head and trunk movement of a subject is visualized by means of markers in the form of incandescent lamps, one each being fitted on either shoulder of the subject and above his forehead and the back of his head. The movement of each marker in the horizontal plane is photographically recorded by a camera, arranged above the subject, under permanent exposure as a luminous trace in what is termed a craniocorpogram. The luminous traces are evaluated on the photograph after the experiment has been carried out. However, the corresponding evaluation of the pictures, which is performed either by measuring the geometry of the luminous traces or by associative connection of the complex movement pattern with comparative patterns denoted as graphic elements is associated with a substantial time outlay. A further disadvantage consists in that some of the information generated in the experiment is lost in the photographic recording of the marker movements, more so since only the horizontal components of the marker movements are to be detected on the photograph. A statement on vertical movements and on the absolute height of a marker in space therefore cannot be made. Moreover, it frequently happens that overlapping of the luminous traces leads to occlusions, since the luminous traces of all the markers are contained on a single photograph. It is therefore difficult or even impossible to characterize individual luminous traces. Information is also lost in the dead angle which is situated directly below the chamber and wherein the chamber projects into the beam path running between the mirror and a marker.

German patent DE 38 29 885 C2 discloses a device wherein use is made, instead of a camera, of an arrangement, fitted above the subject, of photocells for recording the luminous traces. This arrangement eliminates the dead angle. The luminous traces are analyzed there by means of a digital computer, with regard to calculating the movement deviations relevant for craniocorpography. However, no provision is made there for evaluation with regard to an interpretation of acquired movement patterns, in particular of the neck movement pattern.

An apparatus for determining head mobility is described in German utility model DE 295 06 404 U1. Provided for this purpose are a holder, which is fastened on the head of the subject and has three sound transmitters or receivers, and a further three sound transmitters or receivers as reference markers on the body of the subject, in particular on the shoulder, and the travel time of ultrasonic signals between the markers moving with the subject and stationary sound receivers or transmitters is measured. Since it is known that the movements of the upper body of the subject also feature in the measurement results of the head movement, it is possible, in a way not described in more detail, to relate the head positions to the reference markers moved by the body.

SUMMARY OF THE INVENTION

It is accordingly an object of the invention to provide a method and a device for measuring a neck mobility pattern, which overcomes the above-mentioned disadvantages of the heretofore-known devices and methods of this general type and with which the neck movement or neck mobility of the subject can be acquired with particular reliability by comparison with the prior art. In particular, the object of the method is to be able to prove the existence of a cervical column whiplash injury conclusively. A further object is to specify an apparatus which is particularly suitable for carrying out the method.

With the foregoing and other objects in view there is provided, in accordance with the invention, a method for determining the neck movement pattern of a subject, which comprises:

placing markers on the shoulders and on the head of the subject;

recording a head/body movement of the subject with the aid of the markers moving with the body of the subject;

acquiring a locus of each marker in three-dimensional space as a function of time and storing the loci as a data record;

using the data record to form a mean value of the loci representing a shoulder movement and a difference between the mean value and the loci representing a head movement; and generating a profile of the neck movement pattern derived therefrom in at least one space coordinate.

In other words, the neck movement is isolated from the head-body movement acquired without contact, this being done on the basis of craniocorpography by calculating the difference between the trunk movement and the head movement from the acquired loci of the marker also being moved by the subject.

In order to analyze typical neck movement patterns, the first step is to record the loci of markers arranged on the head and on the shoulders and moving with the subject, doing so in three dimensions and as a function of time. Subsequently, the locus representing the head movement is subtracted from the loci representing the shoulder movements, and thus the trunk movement (cervical subtraction kinesimetry). In this process, an average value movement of the two shoulders, and thus a movement of the virtual subpoint of the cervical column, is determined from the loci of the two shoulder movements. The locus of preferably the marker arranged on or over the forehead of the subject is subtracted from this movement of the virtual subpoint of the cervical column. It is also possible, in turn, firstly to determine the mean value from the loci of a marker arranged on or over the forehead and on or above the back of the head, preferably in the region of the continuation of the cervical column supporting point of the head through the head socket joint of the subject. Here, this mean value represents the head movement to be subtracted from the mean value movement of the shoulders.

The invention proceeds in this case from the consideration that, on the one hand, both the seated subject and the subject who is standing, walking or marking time executes whole body sways which are displayed or visible both on the trunk and thus on both shoulders as well as on the head. On the other hand, all movements which occur in the same way on the head and on the trunk are not neck movements. Thus, if the head movements are subtracted from the shoulder-trunk movements, the result from the difference is a movement pattern which is related exclusively to the neck movements and whose time profile in three-dimensional space can be imaged or can be displayed both with reference to the point on the forehead and with reference to the point on the back of the head. This time-dependent, three-dimensional movement pattern can then be projected in terms of data for the purpose of analysis onto the various datum planes, for example of a Cartesian coordinate system. These then two-dimensional profiles of the neck movement pattern, for example in the xy-and/or yz-planes, can then be used to deduce the nature, the degree and, advantageously, also the location of an injury to the cervical column from deviations from profiles of an uninjured cervical column. It is also advantageously possible to determine an injury in the functional movement pattern of the head socket joint.

The localization of an injury of the cervical column is, in particular, of substantial importance for proving a causality of an injury to the cervical column as a consequence of a cervical column whiplash injury caused by a traffic accident: if, on the one hand, it is possible to localize an injury to the cervical column exactly and if, on the other hand, it can be demonstrated that injuries to the cervical column as a consequence of a cervical column whiplash injury occur typically at a very specific point on the cervical column, the desired causality could be proven reliably. On the basis of the considerations and findings explained below, this presupposes that the neck movement is isolated reliably from head and trunk movements in order to be able exclusively to analyze typical neck movements or neck movement patterns with regard to the causality to be proven.

The human spine or the backbone is the axial skeleton which is known to be formed from seven cervical vertebrae, twelve thoracic vertebrae, five lumbar vertebrae, five sacral vertebrae and five coccygeal vertebrae. These vertebrae are interconnected by joints, intervertebral disks and ligaments to form a resilient axial rod structure. In this case, the cervical column constitutes the upper and most mobile part of the entire spinal column with a physiological anterior curvature or lordosis. The seven vertebrae of the cervical column are usually denoted by C1 to C7, C1 being the uppermost vertebra, also called the atlas, below which the vertebra C2, also called the axis, is situated. Cervical vertebrae C3 to C7 situated below are delimited from one another and interconnected by intervertebral disks, while such intervertebral disks are lacking between the cranial base and the two upper cervical vertebrae (C0/C1, C1/C2).

The first cervical vertebra C1 has no intravertebral body and comprises two arches each having a lateral massa supporting the articular surface, and each having a short transverse process with relatively large transverse process foramina. Projecting into the front part of the semicircular canal lumen is a peg, what is termed the dens axis, which rotatably clamps the head cap with the spinal column. The second cervical vertebra C2 (axis or epistropheus) constitutes the axis of rotation for the first cervical vertebra C1 (atlas) including the head. It comprises a process, what is termed the dens, which projects like a pin toward the atlas from the vertebral body, and in each case two lateral upper and lower articular surfaces.

A head-neck mobility which can easily be controlled by the human brain is required for orientating the head and the line of vision both for seated and for standing subjects. The three head socket joints serve chiefly for these movements of the head. The first and upper head joint (articulatio atlanto-occipitalis) is a paired joint with elliptically shaped joint bodies between the condyles of the occipital bone, also denoted as C0, and the upper lateral articular surfaces of the atlas (C1). This joint is used predominantly for the nodding movements, the forwardly thrusting head movements and the lateral inclination of the head. The second, lower head joint (articulatio atlanto-axialis) is composed, in turn, of two joint units which are, however, different. It is therefore a multiple joint between the first and second cervical vertebral bodies. While one of the two joint units (articulatio atlanto-axialis mediana) takes over the rotation of the head, a sliding tilting of the head takes place in the second joint unit (articulatio atlanto-lateralis).

The cervical column can therefore be regarded as a unit, but breaks down for anatomical reasons into two movement structures, specifically the head socket joint with the sliding and rotary movement segments C0, C1 and C2, which lack intervertebral disks, and the further segment connections in the manner of a resilient rod with movement-restricting intervertebral disks between the vertebral bodies C2 to C7 and, farther to Th1.

The turning to the side or forward or backward that is important for orientating the head in space can, however, in the case of a stiff or injured neck, also be taken over by other sections of the spinal column, for example by the thoracic and lumbar vertebrae, or by the hip joints, and from the lower extremities. A forward, sideward or backward movement or rotary movement actually performed by the head and detected there can therefore also be undertaken by deeper control members of the body. In other words: in order to prove the causal injury of the neck movement apparatus in the region of the head socket joint there is a need always to take into account that the relevant subject can effect head movements that are to be controlled simultaneously not only from the neck, but with the assistance of the entire body, the hip joints, the joints of the legs, and also the thoracic and lumbar vertebrae, as it were in a system of a second and third loop. The neck movements must therefore be isolated from the movements of the remainder of the body in order to determine an actual injury in the head socket joint and in the cervical column.

Motor disturbances caused exclusively at the neck can be acquired by measurement and evaluated by data processing in a reliable fashion by means of the method, developed further on the basis of craniocorpography, for determining the neck movement of a subject, in the case of which loci recorded by means of markers arranged on the two shoulders and on the head of the subject are subtracted from one another in order to isolate the neck movement in the way described. A further differentiation is based on subtracting the movement of the occipital pole from the trunk movement pattern in comparison with the movement subtraction of the sinciput pole (frontal marker) from the trunk movement pattern. The differentiation of these two loci yields a deduction on the disturbance of the head socket joint. Moreover, loci acquired by markers fitted laterally over the ears on the top of the head can be used, in addition, for differential analysis of transverse sways.

In a corresponding analysis of the determined neck movement patterns, it is possible to make expedient use of reference patterns which are recorded in an appropriate way on uninjured subjects and on subjects who, for example as a consequence of an operation, demonstrably exhibit a localized injury to a specific region of the cervical column. In this case, it may be assumed on the basis of the above considerations and findings that the determined neck movement patterns have always been determined by means of the head socket joint with its three joint parts.

The determined neck movement patterns therefore reproduce a sliding-nodding movement forward by means of the upper head joint, a rotary movement by means of the middle lower head joint, and a lateral inclination and tilting by means of the lateral lower head joint, this movement also being supported by the upper head joint. Like a flexible rod, the section of cervical column situated therebelow between the third and seventh cervical vertebrae (C3 and C7, respectively) adds further adjustments in the three spatial planes. However, these are severely limited in angular terms, since these vertebrae are interconnected by intervertebral disks. There are no intervertebral disks on the vertebral vein C0/C1, that is to say in the region between the underside of the skull and the first cervical vertebra C1 (atlas), nor on the vertebral plane C1/C2, that is to say in the region between the underside of the first cervical vertebra C1 (atlas) and the top side of the second cervical vertebra C2 (axis), and so this joint moves in a particular way.

Investigations carried out using this method have shown that, in patients in whom this articular apparatus is damaged, typical variations in the rotary, sliding and tilting movements can be reliably represented as a function of the type of injury of the ligaments and joints. It was possible to underpin these findings by virtue of the fact that corresponding, typical joint injuries of the patients examined had been imaged with the aid of a radiological technique using nuclear magnetic resonance imaging. These injuries were additionally verified by neurosurgical inspections of the joint after surgical incision.

The method based on craniocorpography has the substantial advantage of representing injuries, determined rather in the manner of a Lakmus test, after a cervical column whiplash injury in a causal and comprehensible fashion even in the functional field, the determined neck movement pattern being used as a measure of the mobility of the cervical column and, preferably, of the movement variations in the head socket joint. It is ensured in this case that no movements or component movements of the remainder of the body, that is to say the head and/or the trunk, which could falsify the results of measurement or examination, are included in the determined neck movement pattern. The method according to the invention is therefore particularly suitable for detecting said disturbances in the case of the known functional injuries for which there has previously been only a suspicion of damage to the cervical column by the cervical column whiplash injury.

In a particularly expedient refinement, the subtraction between the shoulder movement, and thus the trunk movement, and the head movement is performed in each of the three space coordinates, a two-dimensional movement pattern being generated in each case in the various datum planes of the Cartesian coordinate system. In addition, a projection of the loci representing the movement of at least one shoulder and the head of the subject onto at least one datum plane is preferably used to determine a number of frequencies corresponding to a body sway cycle, and to store them as analyzable and typifiable movement patterns of the corresponding shoulder—and thus the trunk—and/or the head of the subject.

The projections of the loci, or each locus, onto the datum planes of the coordinate system are expediently determined for this purpose from the data record. The loci are advantageously respectively stored as a data field (time-dependent) for this purpose.

With the above and other objects in view there is also provided, in accordance with the invention, an apparatus for evaluating a movement pattern of a subject. The apparatus comprises:

- a plurality of markers respectively disposed on the shoulders and on the head of the subject;
- a data processing system connected to a receiver configuration for recording a locus of each of the markers, the data processing system comprising a processing stage for calculating a data record, representing the locus, from signals of the receiver configuration;
- the data processing system further comprising an analysis module with a subtraction stage configured to use the data record to form a difference between a mean value of the loci representing movements of the shoulder and a locus representing the head movement, and generating a profile of a neck movement pattern derived therefrom in at least one of three space coordinates.

In other words, the apparatus has a data processing system which is connected to a receiver configuration for recording the locus of each marker and which comprises a processing stage for calculating the data record, representing the loci, from the signals of the receiver configuration. Arranged downstream of this processing stage is a subtraction stage which uses the data record to form the difference between the mean value of the two loci representing the shoulder movement and the locus representing the head movement, and generates the profile of the neck movement pattern derived therefrom in the, or in each of the, three space coordinates.

The receiver configuration expediently comprises two receivers arranged at right angles to one another. The receivers can be ultrasound transducers, CCD cameras (video cameras), photoelements or the like which are arranged distributed relative to one another in space and serve to record and, if appropriate, preprocess acoustic or optical signals. Owing to the arrangement of the receivers at right angles to one another, the loci of the markers are recorded in at least two different planes, for example in the xy-plane and in the yz-plane or in the xz-plane. The coordinates of the loci with reference to the third plane can then be calculated from the measured data of the two receivers. When ultrasound is used instead of light for marking purposes, the measurement can also be carried out in a non-darkened space.

Arranged downstream of the processing stage for the purpose of storing the data acquired in the current measurement is a database wherein reference data records determined in a multiplicity of reference measurements are preferably also stored. An analysis module or an analysis stage of the data processing system can then use the currently acquired data record and the corresponding reference data record to determine a number of characteristics or reference valves which are used in a comparison module or in a comparison stage in the manner of data recognition to determine the degree of correspondence between the data records. The data processing system can then subsequently assign to each data record an identifier corresponding to an injury or trauma, and transfer the data record with the aid of the identifier to the data base for the purpose of expanding the corresponding reference data record.

The processing stage assigns the locus of each marker to the data record, expediently as a data field. A matrix with a number of data fields corresponding to the number of the markers is thereby provided, each data field including the three space coordinates referred to a Cartesian coordinate system at the respective instant. A temporary data record memory for buffering the acquired measured data is advantageously arranged downstream of the processing stage.

The advantages achieved with the aid of the invention consist, in particular, in that a reliable statement on a degree, the extent and the location of an injury or trauma to the cervical column of a subject can be made from a computer-assisted evaluation of the measured data acquired for a number of optically or acoustically acquired movements, and the neck movement patterns, derived therefrom by subtracting the shoulder and head movements, with the aid of corresponding curves. Whereas the measured data are acquired virtually without contact on the body of the subject, the evaluation is performed in a data processing system which is detached from the body of the subject and wherein the measured data are processed outside the body and conditioned for analyzing the neck movement patterns. In addition, it is possible in appropriate representations of the loci to distinguish between summary head-neck movements and the body and trunk movements, as well as between head movement (rotation, nodding) and neck movements.

The evaluation of the neck movement patterns both of healthy and of pathological cervical column movements on the one hand permits the application of a knowledge base with a number of reference data and reference patterns with the aid of which currently acquired and non-diagnozed neck movement patterns can be assigned to known injuries and types of trauma. On the other hand, it is possible thereby and with the aid of the neck movement patterns to make even qualitative and quantitative as well as, in particular, comprehensible statements on a possible causal relationship between the disturbances, and to use them as proof or evidence of a cervical column whiplash injury, in particular one caused by an accident.

Other features which are considered as characteristic for the invention are set forth in the appended claims.

Although the invention is illustrated and described herein as embodied in a method and apparatus for determining the neck movement pattern, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIGS. 2 to 5 (each with four sub-figures) show head and shoulder movement patterns in a projection onto the yz-plane (left-hand top and bottom half) and onto the xy-plane (right-hand top and bottom half);

FIGS. 6 to 9 are graphs showing, in an amplitude-time scheme, differential movement patterns of the neck movements corresponding to the movement patterns in accordance with FIGS. 2 to 5, in the three space coordinates x, y, z; and FIG. 10 is a graph showing a further neck movement pattern in an illustration similar to FIGS. 6 to 9.

DESCRIPTION OF THE PREFERRED EMBODIMENTS

Figure 1:
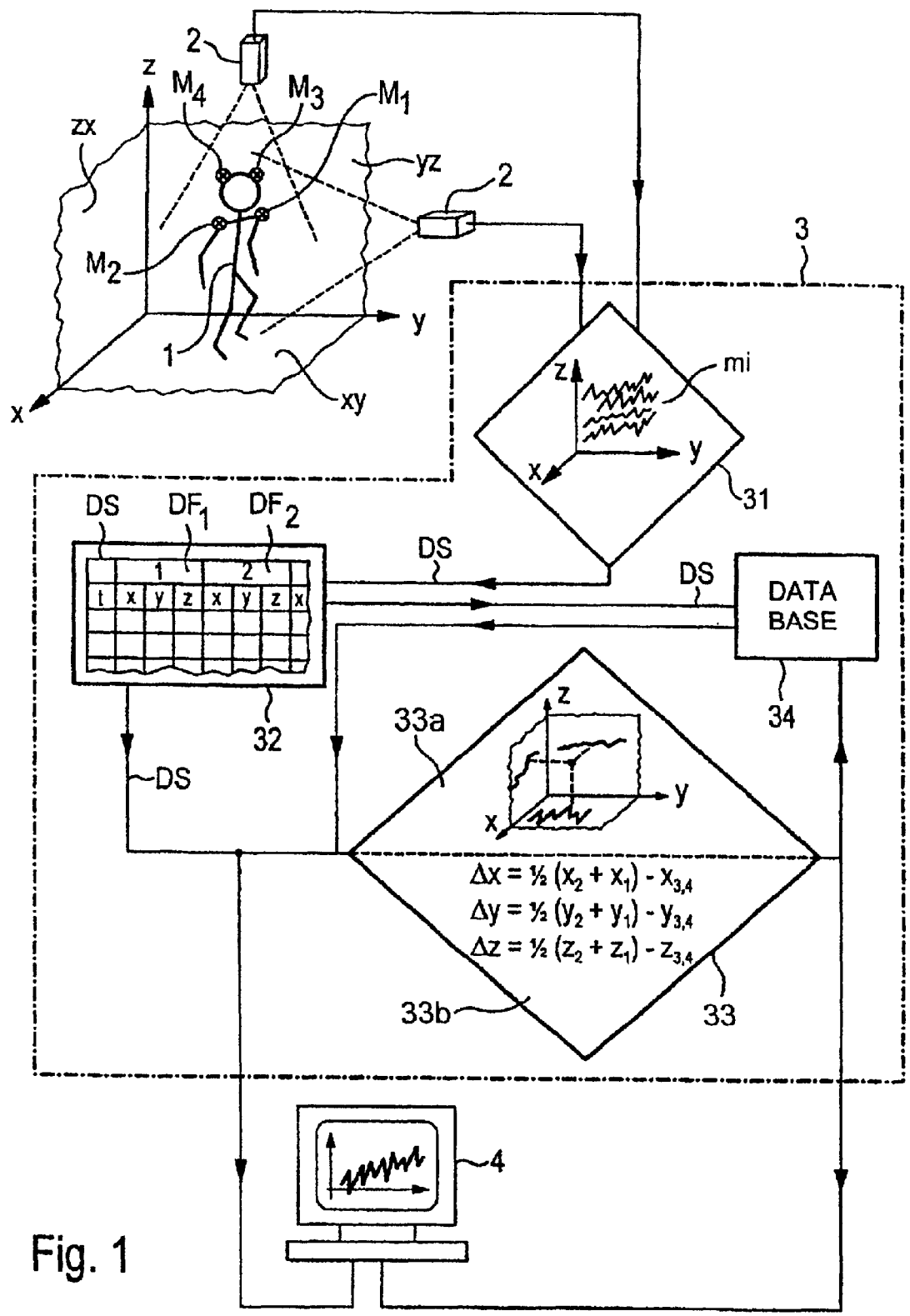
FIG. 1 is a schematic diagram of an apparatus having components provided for evaluating a movement pattern.

Referring now to the figures of the drawing in detail and first, particularly, to FIG. 1 thereof, there are shown two receivers 2 aligned orthogonally relative to one another and provided for the purpose of acquiring the head-body movement patterns of a subject 1. The receivers 2 receive signals from a number of markers $M_i$ moving along with the subject 1. The visualization of the body movement can be implemented with particular ease in an optical way. In this case, use is made of incandescent lamps or light-emitting diodes as markers $M_i$ and, correspondingly, one camera each, such as a video camera, for example, as receiver 2. The movement pattern can also be marked by ultrasonic transmitters as markers $M_i$ and ultrasonic receivers as receivers 2. Alternatively, it is also possible to use passive markers $M_i$ which merely reflect the signal emitted by an external source. As is usual in what is termed craniocorpography (CCG or UCCG), in this case the observation is expediently limited to the head and shoulder movement of the subject 1. For this purpose, one marker $M_1$ and $M_2$ each is fitted on or over the left-hand shoulder and on or over the right-hand shoulder of the subject 1, and one further marker $M_3$ and $M_4$ each is fitted on or over the forehead of the subject and on or over the back of his head.

The receivers 2 in each case feed a two-dimensional image of the movement of the markers $M_i$ to a processing stage 31 which is included in a data processing system 3 and uses the images transmitted by the receivers 2 to determine the loci $m_i$ of each marker $M_i$ in three-dimensional space as a function of time t. The space coordinates of each locus $m_i$ are presented in a Cartesian coordinate system x,y,z, the initial position of the subject 1 being assigned to the origin, and the x-axis thereby corresponding to the lateral axis. The y-axis then runs horizontally in the walking direction of the subject 1, while the z-axis extends vertically upward. The datum planes of the coordinate system, which are formed by the respective axes, are the xy-plane (horizontal), the yz-plane (longitudinally vertical) and the zx-plane (laterally vertical).

The calculation of the locus $m_i$ of each marker $M_i$ is performed by means of the data processing system 3 with the aid of an algorithm of the processing stage 31. If an analog recording technique is used for the receivers 2, a conversion from analog data into digital data firstly takes place in the processing stage 31. The processing stage 31 transfers the loci $m_i$ as a data record DS to a preferably temporary data memory 32. The latter is divided in this case into data fields $DF_i$. A data field $DF_i$ represents the locus $m_i$ of a marker $M_i$.

The data memory 32 makes the data record DS available to an analysis module 33, which is implemented in the form of software and has an imaging stage 33a and a subtraction stage 33b. Moreover, the data record DS is stored in a database 34. The imaging stage 33a produces a projection of the loci $m_i$ onto the datum planes xy, yz and zx in each case by selecting data from the data record DS. Since the loci $m_i$ typically have a periodic structure caused by a body sway, an algorithm of the analysis module 33 carries out a subdivision of the loci $m_i$ into periodic sequences. Such a sequence, whose start and end is marked in each case by a sharp change in direction of the locus $m_i$, corresponds in this case exactly to one cycle of the body sway. A number of characteristics and parameters can be derived in a way not represented in more detail by further algorithms of the analysis module 33 from the loci $m_i$ projected onto the datum planes xy (horizontal plane), yz (longitudinal-vertical plane) and zx (lateral-vertical plane) and subdivided into sequences.

The projections of the loci $m_i$ onto the xy-plane and onto the yz-plane are preferably measured geometrically and physically in order to evaluate typical shoulder and head movement patterns. Corresponding movement patterns are illustrated in FIGS. 2 to 5. These figures respectively show in the top half of the sheet a movement pattern for a point on the forehead which was generated during a sequence of steps by the respective subject 1, and an associated movement pattern of the right shoulder in the bottom half of the figure in each case. The left half of the figure respectively corresponds in this case to the yz plane, while the right half of the figure respectively shows a representation in the xy-plane.

Because of the periodic structure of each locus $m_i$, the relevant parameters are the amplitude, the period, the frequency of a sway and the distance (step size) covered during a sway period in and transverse to the direction of sway. These parameters can both be determined from a single sequence (single-step analysis) and be derived statistically from a number of sequences and specified in the form of a mean value and standard deviation (whole-reaction analysis).

Moreover, irregularities in the body sway can be quantified by specifying an amplitude distribution and a frequency distribution obtained by means of spectral analysis (Fourier transformation). Moreover, physical parameters and characteristics can be determined from the centroid movement of the body, the rotation of the body in space and the rotation of the head relative to the trunk. The loci $m_i$ of a plurality of markers $M_i$ can also be combined with one another for this purpose.

By selection from the data record DS, the subtraction stage 33b forms the difference between the shoulder movement represented by the corresponding loci $m_i$ and the head movement acquired at the same time. In this case, the mean value is firstly formed from the acquired loci $m_2$ and $m_1$ of the right-hand and the left-hand shoulder markers $M_2$ and $M_3$, respectively. This mean value profile of the shoulder and thus the trunk movement therefore represents the virtual subpoint of the cervical column of the subject 1. The neck movement or mobility of the cervical column of the subject 1 thereby isolated from head and shoulder or trunk movements is yielded by subtracting the head movement from this mean value. Only the locus $m_3$ of the forehead marker $M_3$, for example, can be used for this purpose. Alternatively, the head movement can be calculated by the subtraction stage 33b by averaging the loci $m_3$ and $m_4$ of the forehead marker $M_3$ or marker at the back of the head $M_4$. The subtraction and thus the isolation of the neck movement pattern from the acquired head-body movement (craniocorpogram) is yielded for each of the three space coordinates in accordance with the relationships:

$$\Delta x = \frac{1}{2}(x_2 + x_1) - x_{3,4} = \frac{1}{2}(x_{rS} + x_{lS}) - x_K$$

$$\Delta y = \frac{1}{2}(y_2 + y_1) - y_{3,4} = \frac{1}{2}(y_{rS} + y_{lS}) - y_K$$

$$\Delta z = \frac{1}{2}(z_2 + z_1) - z_{3,4} = \frac{1}{2}(z_{rS} + z_{lS}) - z_K$$

Here, the respective minuend represents the profile of the mean value of the shoulder movements (right shoulder rS, left shoulder lS), and thus the profile of the virtual subpoint of the cervical column, while the subtrahend characterizes the profile of the head movement (head K), for example likewise as mean value.

The corresponding profiles of the neck movement patterns $\Delta x$, $\Delta y$, $\Delta z$ in the three space coordinates are shown by FIGS. 6 to 9, $\Delta x$ representing the lateral, $\Delta y$ the anterior-posterior, and $\Delta z$ the vertical/cervical neck movement patterns. The neck movement patterns of FIGS. 6 to 9 determined by the described subtraction method (cervical subtraction kinesimetry) were determined from the loci $m_i$ and data records DS on which FIGS. 2 to 5 are based.

FIGS. 2 and 6 show spatial/temporal measurement diagrams of 3D measurements of the loci $m_i$, of the head movements (FIG. 2 top) acquired on the forehead, and of the movement of the right shoulder (FIG. 2 bottom) or neck movements derived therefrom in three direction-time planes of a 54-year-old man after a head-neck whiplash injury. In this case, the left-hand top diagram and the right-hand bottom diagram in FIG. 2 respectively represent a projection of the locus $M_3$ or $m_2$ onto the yz-plane, while the right-hand top and bottom diagrams represent a projection of the respective locus $m_3$ or $m_2$ onto the yz-plane.

The profile of the projected locus $m_2$ in the right-hand bottom half of FIG. 2 shows, the corresponding xy movement analysis of the right shoulder, normal step cycles of approximately 2¼ Pi as an expression of the periodicity, as presented by means of the circular function, of the step movement in the course of two seconds. A striking feature of the yz representation in accordance with the left-hand bottom half of FIG. 2 is that certain vertical irregularities occur during the step cycles. The subtraction for isolating the neck movement or the neck movement pattern is performed using the stated relationships for $\Delta x$, $\Delta y$, $\Delta z$.

Using the profiles in the associated FIG. 6, which are determined with the aid of the subtraction analysis of the neck movement, the amplitude-time movement pattern $\Delta y$ shows a strongly dysrhythmic neck movement pattern, which has disturbed head nodding and head sliding movements in the y-coordinate. This pattern indicates a clear disturbance in the head socket joint. In this case, the y-coordinate represents the head nodding movements, that is to say the anterior-posterior movements, while the x-coordinate represents the lateral movements and transverse variations. The vertical movements, that is to say the stamping movements, are represented by means of the z-coordinate.

Figure 7:
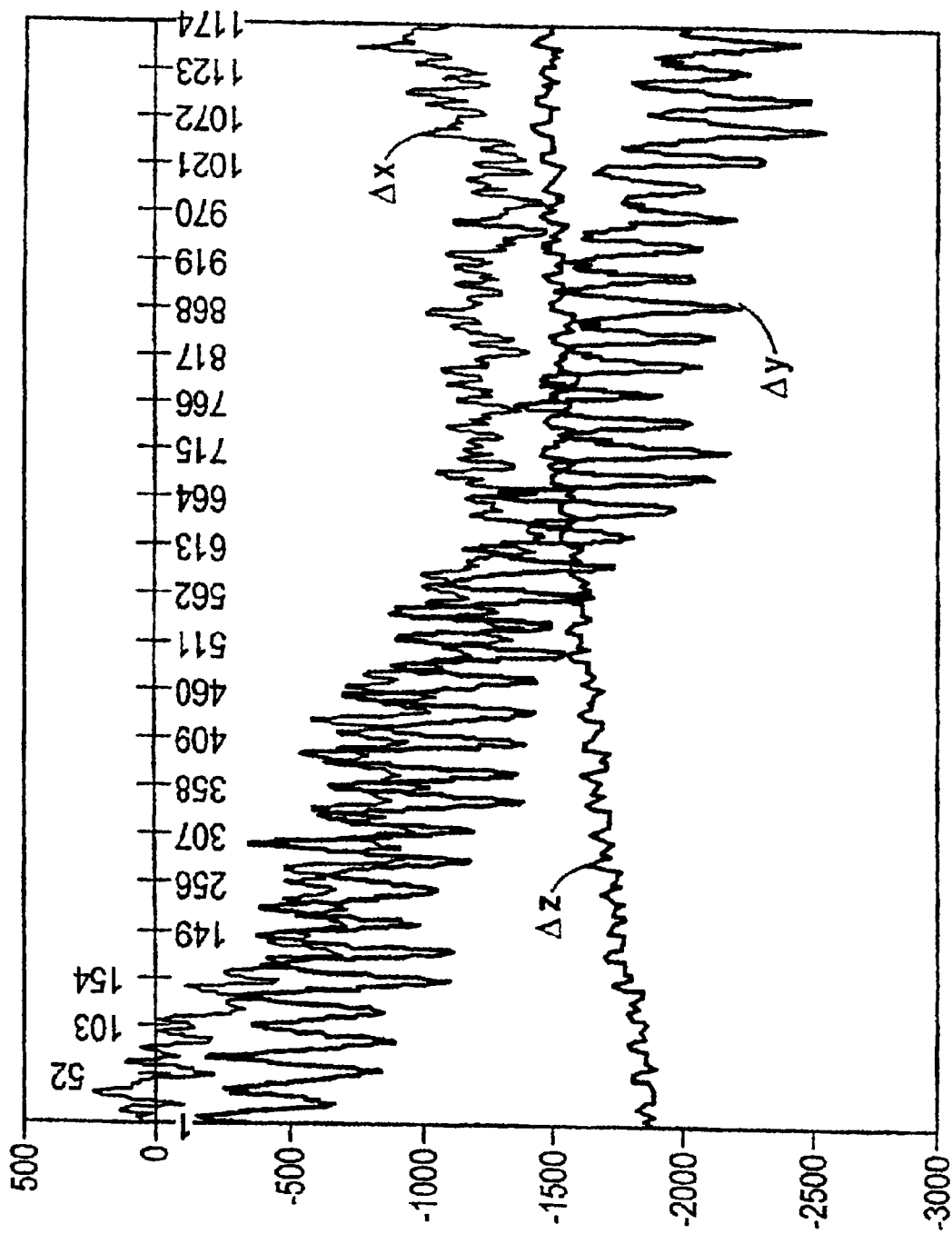

FIGS. 3 and 7 show spatial/temporal measurement diagrams of 3D measurements of the loci $m_i$ of the head movements at the forehead (FIG. 3 top) and at the right shoulder (FIG. 3 bottom), and neck movements derived therefrom in three direction-time planes of a 60-year-old man with the complaint of central vertigo. In this case, the left-hand top and bottom diagrams in FIG. 3 respectively represent a projection of the locus $m_3$ or $m_2$ onto the yz-plane, while the right-hand top and bottom diagrams represent a projection of the respective locus $m_3$ or $m_2$ onto the yz-plane. The yz- and xy-representations in accordance with FIG. 3 show regular step cycles of 2Pi in the course of two seconds. Coarsened sways in the nodding axis y are shown by the subtraction analysis of the head movements with the aid of the difference profile $\Delta y$ according to FIG. 7. A striking feature is the irregular transverse variation pattern $\Delta x$, as well as the raising and lowering pattern $\Delta z$ of the head in the z-coordinate during the individual step cycles.

Figure 8:
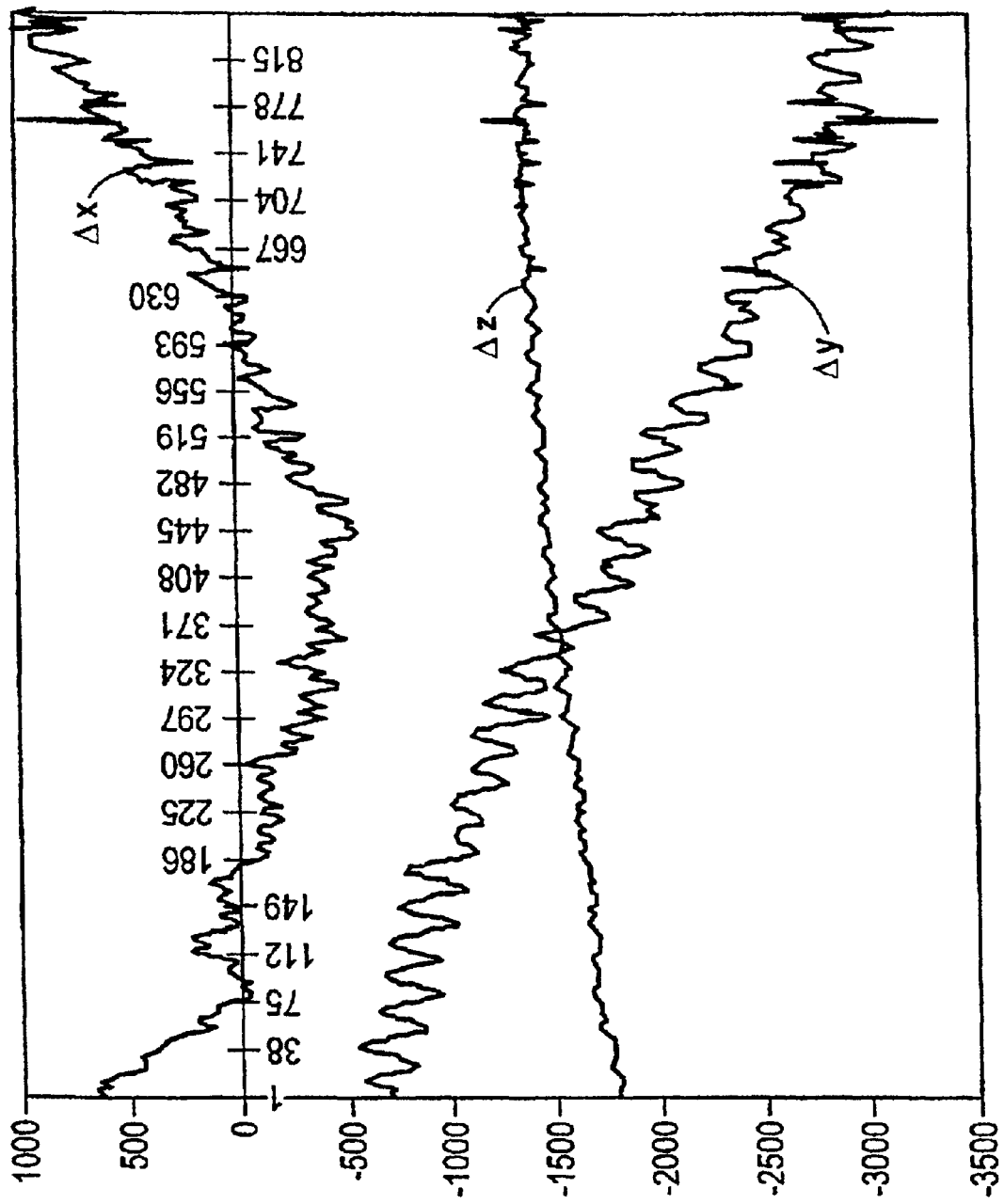

FIGS. 4 and 8 show spatial/temporal measurement diagrams of 3D measurements of the loci $m_i$ of the head movements at the forehead (FIG. 4 top) and at the right shoulder (FIG. 4 bottom) and neck movements derived therefrom in three direction-time planes of a 63-year-old man in the case of combined statoacoustic disturbances, that is to say in the case of multiple neurosensory disturbances of the inner ear in the auditory and balancing section. In this case, the left-hand top and bottom diagrams in FIG. 4 respectively represent a projection of the locus $m_3$ or $m_2$ onto the yz plane, while the right-hand top and bottom diagrams represent a projection of the respective locus $m_3$ or $m_2$ onto the yz plane. An irregular and constricted movement pattern is to be observed with reference to the head and the shoulder, respectively, in the yz representation in accordance with the top and bottom right-hand half of FIG. 4, while the xy representation in accordance with the right-hand half of the Fig. shows a regular step cycle pattern over 3 Pi. The subtraction analysis of the neck movement patterns in accordance with FIG. 8 shows an only slightly disturbed picture of the step cycles on the head nodding axis $\Delta y$. The transverse variation axis of the head is irregular and denoted by a dysrhythmic movement pattern $\Delta x$. The vertical movement, that is to say the upward and downward movement pattern $\Delta z$, is substantially normal in the amplitude-time representation.

Figure 9:
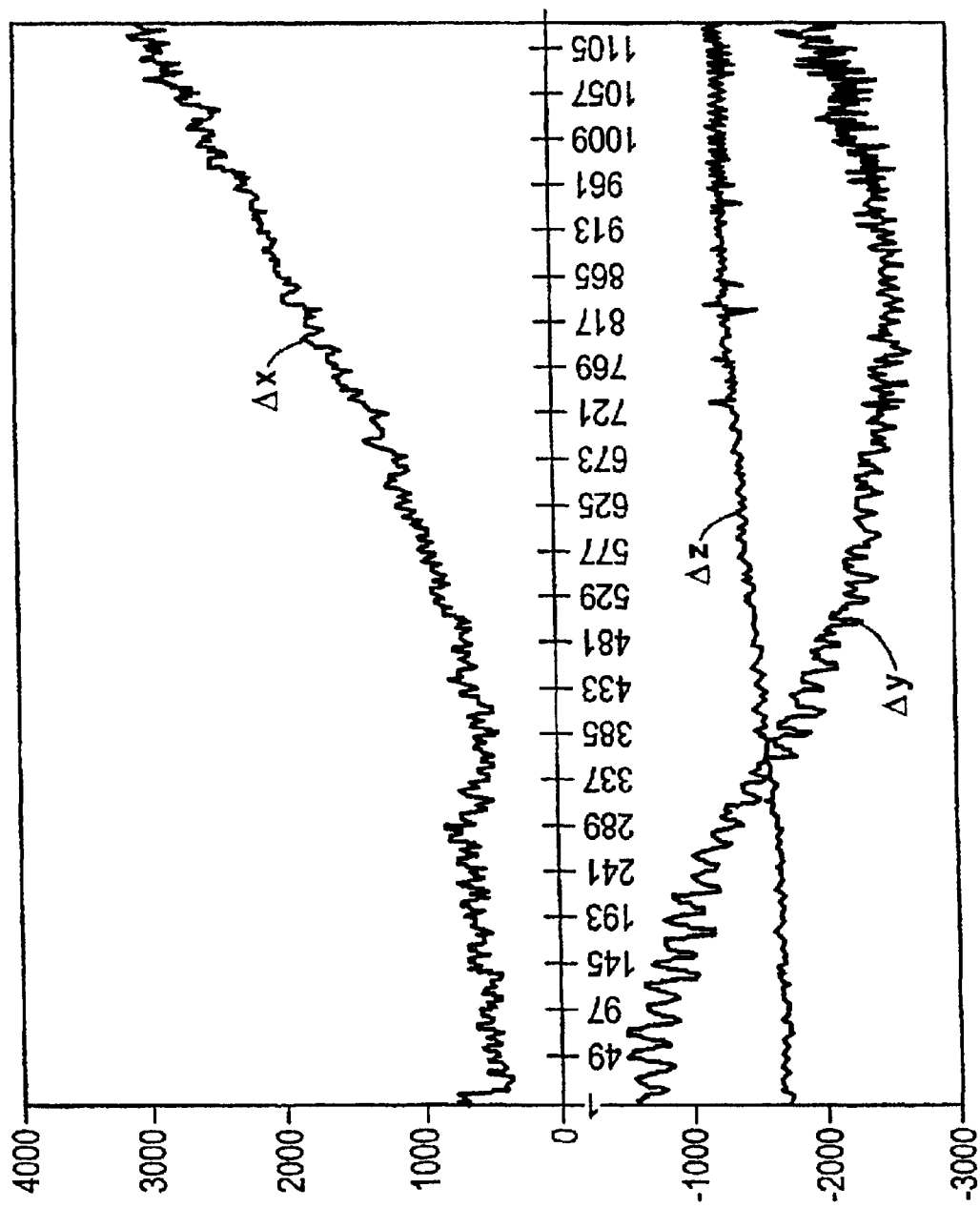

FIGS. 5 and 9 show spatial/temporal measurement diagrams of 3D measurements of the loci $m_i$ of the head movements at the forehead (FIG. 5 top) and at the right shoulder (FIG. 5 bottom) as well as neck movements derived therefrom in three direction-time planes of a 25-year-old woman after cervical column whiplash injury. Here, the left-hand top and bottom diagrams in FIG. 5 respectively represent a projection of the locus $m_3$ or $m_2$ onto the yz-plane, while the right-hand top and bottom diagrams represent a projection of the respective locus $m_3$ or $m_2$ onto the yz-plane. In accordance with FIG. 5, while marking time (stepping test), this subject 1 images approximately 4 Pi in the course of two seconds. In accordance with FIG. 9, the subtraction analysis of the neck movements shows a constricted movement pattern $\Delta y$ on the head nodding axis. The transverse variations $\Delta x$ are also strikingly constrained. The vertical head movements are stable according to the $\Delta z$ profile. This neck movement pattern characterizes what is termed a "stiff neck" with a striking constraint of head movement.

Referring now to FIG. 10, there is shown, in a representation similar to FIGS. 6 to 9, the state of a 47-year-old man with the complaint of tinnitus, that is to say noise disturbances of the inner ear. The step cycle pattern of the subtraction analysis of the neck movements shows a regular $\Delta y$ movement pattern which in this form serves, in particular, to stabilize the balance of the eyes by pushing, lowering and raising the head.

In addition to the physical and/or geometric characterization, it is also possible, for example, to determine the correspondence between the linear form of the loci $m_1$ and comparison or reference patterns stored in the database 34. An appropriate comparison can be referred to an individual sequence or to the entire locus $m_i$. In this case, variation sequences can be wherein with the aid of the shape and possible reversal regions. Arcuate, loop or pointed reversal regions are typical in this case. The contour shape of the surface swept over by a projection of a locus $m_i$ can be used to describe the overall locus $m_i$.

A reference data record, which has a data structure corresponding to the data record DS and is created in a reference measurement by analogy with creation of the current data record DS, is made available to the analysis module 33 from the database in order to evaluate the data record DS. The data processing system 3 determines the degree of correspondence between the data records from the reference data record by comparison with the current data record DS. A current movement pattern can then be typified or at least qualitatively specified with the aid of a direct or indirect pattern comparison.

The analysis module 33 is connected to an output module 4, for example a display screen, a printer or a plotter, in order to output the head and shoulder movement patterns and the neck movement pattern. Furthermore, the movement pattern stored in the data record memory 32 in the form of the data record DS can be output via this output module 4.

I claim:

1. A method for determining the neck movement pattern of a subject, which comprises:
   placing markers on the shoulders and on the head of the subject;
   recording a head/body movement of the subject with the aid of the markers moving with the body of the subject;
   acquiring a locus of each marker in three-dimensional space as a function of time and storing the loci as a data record;
   using the data record to form a mean value of the loci representing a shoulder movement and a difference between the mean value and the loci representing a head movement; and
   generating a profile of the neck movement pattern derived therefrom in at least one space coordinate.

2. The method according to claim 1, which comprises forming the difference in each of three space coordinates, and generating a two-dimensional movement pattern.

3. The method according to claim 1, which comprises determining from the data record a projection of the locus onto the datum plane of a Cartesian coordinate system.

4. The method according to claim 1, which comprises determining from the data record a projection of each locus onto the datum plane of a Cartesian coordinate system.

5. The method according to claim 1, which comprises determining a resulting head movement from the mean value of the loci representing the movements of a marker moving with the forehead of the subject and a marker moving with the back of the head of the subject.

6. The method according to claim 1, which comprises determining a degree of agreement between a number of appropriately determined difference patterns stored as reference and a current difference pattern of the neck movement.

7. An apparatus for evaluating a movement pattern of a subject having shoulders and a head, comprising:
   a plurality of markers respectively disposed on the shoulders and on the head of the subject;
   a data processing system connected to a receiver configuration for recording a locus of each of said markers, said data processing system comprising a processing stage for calculating a data record, representing the locus, from signals of the receiver configuration;
   said data processing system further comprising an analysis module with a subtraction stage configured to use the data record to form a difference between a mean value of the loci representing movements of the shoulder and a locus representing the head movement, and generating a profile of a neck movement pattern derived therefrom in at least one of three space coordinates.

8. The apparatus according to claim 7, wherein said receiver configuration comprises two receivers disposed orthogonally relative to one another.

9. The apparatus according to claim 7, wherein said processing stage is configured to assign the locus of each marker as a data field to the data record.

10. The apparatus according to claim 7, which further comprises a temporary data record memory arranged downstream of the processing stage in a signal processing direction.

11. The apparatus according to claim 7, which further comprises an output module connected to receive from said data processing system the profile of the neck movement pattern determined by the subtraction for displaying the movement pattern.

* * * * *